United States Patent [19]

Cronin

[11] 4,141,716

[45] Feb. 27, 1979

[54] METHOD FOR INCREASING YIELD OF SOY BEANS

[75] Inventor: Christopher H. Cronin, Cambridge, England

[73] Assignee: Fisons Limited, England

[21] Appl. No.: 790,134

[22] Filed: Apr. 22, 1977

Related U.S. Application Data

[63] Continuation-in-part of Ser. No. 655,612, Feb. 5, 1976, abandoned.

[30] Foreign Application Priority Data

Feb. 12, 1975 [GB] United Kingdom ............... 5905/75
May 27, 1975 [GB] United Kingdom ............. 23187/75

[51] Int. Cl.$^2$ ............................................. A01N 9/12

[52] U.S. Cl. ....................................................... 71/90
[58] Field of Search ........................................... 71/90

[56] References Cited

U.S. PATENT DOCUMENTS 3,770,754  11/1973  Parsons .................. 260/302 SD

*Primary Examiner*—Joseph Paul Brust
*Attorney, Agent, or Firm*—Wenderoth, Lind & Ponack

[57] ABSTRACT

There is provided a method of regulation of the growth of a crop of soya beans, in which (3-phenyl-1,2,4-thiadiazol-5-ylthio)acetic acid or a functional derivative thereof is applied to the locus at which the crop is growing.

11 Claims, No Drawings

METHOD FOR INCREASING YIELD OF SOY BEANS

This is a continuation-in-part of Ser. No. 655,612, filed Feb. 5, 1976 now abandoned.

This invention concerns a method of plant growth regulation.

(3-phenyl-1,2,4-thiadiazol-5-ylthio) acetic acid is a known compound, but hitherto its surprisingly good plant growth regulant activity with respect to soya beans (Glycine spp) has not been appreciated.

In one aspect, therefore, this invention provides a method of regulation of the growth of a crop of soya beans, in which (3-phenyl-1,2,4-thiadiazol-5-ylthio) acetic acid or a functional derivative thereof is applied to the locus at which the crop is growing, in an amount sufficient to exert its plant growth regulant effect.

For convenience of use, water-soluble salts of (3-phenyl-1,2,4-thiadiazol-5-ylthio) acetic acid are preferred, eg alkali-metal salts or salts with amines, and especially the sodium, triethylamine, tributylamine, diethanolamine and triethanolamine salts. Alternatively, the free acid, or esters (especially those formed with alkanols of 1 to 10, preferably 5 to 9, carbon atoms, for example the heptyl, 1-methylheptyl and nonyl esters), or the amide thereof may be employed.

The active compound is preferably applied to the crop at a rate of from 1 oz to 4 lbs per acre, rates of 2 oz to 1 lb/acre, and more especially 4 oz to 8 oz/acre, being most preferred.

For application, the active compound is preferably formulated into an appropriate composition with a suitable vehicle. Thus, the compound may, for example, be formulated into a solution or suspension in an appropriate liquid medium, or into a wettable powder by admixture with a wetting agent and, if desired, an inert diluent. Suitable liquid media include water (in which case the compositions preferably also contain a wetting agent) and water-immiscible solvents, for example high boiling hydrocarbons, suitably containing dissolved emulsifying agents so that the composition acts as a self-emulsifiable oil on addition to water.

Inert diluents with which the compound may be admixed to form a powder include powdered or finely-divided solid materials such as clays, sands, talc, mica, peat, fertilizers and soil. If desired, the compound may be used to impregnate or coat preformed granules of, for example, peat or limestone.

The wetting agents used may comprise anionic compounds such as soaps, fatty sulphate esters, such as dodecyl sodium sulphate, fatty aromatic sulphonates, such as alkylbenzene sulphonates or butyl naphthalene sulphonates, or more complex fatty sulphonates, such as the amide condensation product of oleic acid and N-methyl taurine or the sodium sulphonate of dioctyl succinate.

The wetting agents may alternatively comprise non-ionic wetting agents, for example condensation products of fatty acids, fatty alcohols or fatty substituted phenols with ethylene oxide, or fatty esters of sugars or polyhydric alcohols, or the products obtained from the latter by condensation with ethylene oxide, or block copolymers of ethylene oxide and propylene oxide.

The wetting agents may also comprise cationic agents, for example cetyl trimethylammonium bromide.

The compositions which are employed may contain other active materials in addition to the plant growth regulants defined hereinbefore, for example other plant growth regulants, such as 2,3,5-triiodobenzoic acid, (2-chloroethyl)phosphonic acid, N-1-naphthylphthalamic acid, or morphactins, for example 2-chloro-9-hydroxyfluorene-9-carboxylic acid (methyl ester) or 9-hydroxy-fluorene-9-carboxylic acid (butyl ester), pesticides, such as dichloro-diphenyl-trichloroethane, carbaryl or dimethoate; herbicides, for example 2,4-dichlorophenoxy-acetic acid, 2-methyl-4-chlorophenoxyacetic acid, or substituted triazines or ureas; or fungicides, such as copper compounds or dithiocarbamates.

The compositions which are employed are conveniently produced initially as concentrates for dilution before application. Such concentrates conveniently contain from 0.5 to 80% by weight, for example from 10 to 50% by weight of the plant growth regulants defined hereinbefore.

The compositions are preferably applied post-emergence, and may be applied by any method appropriate to the particular formulation employed, for example spraying.

The invention is further described, though only by way of illustration, in the following Examples.

EXAMPLE 1

A 25% w/v formulation of (3-phenyl-1,2,4-thiadiazol-5-ylthio) acetic acid was prepared from the following:

| | |
|---|---|
| (3-phenyl-1,2,4-thiadiazol-5-ylthio)acetic acid | 250 g |
| triethanolamine | 150 g |
| n-butanol | 100 ml |
| water (to 1 liter) | approx 600 ml |

EXAMPLE 2

Wayne and Beeson soyabeans were planted in plots in 30-inch rows on irrigated level benches. The plots were 30 feet long by 4 rows wide, and six replications were made. When the plants had reached the 5–6 leaf stage, they were sprayed with an aqueous dilution of the formulation of Example 1 at a rate of 8.0 oz/acre of (3-phenyl-1,2,4-thiadiazol-5-ylthio) acetic acid. The results obtained (yield in bushels/acre) compared with control plots which were not so treated were as follows:

| | Yield (bushels/acre) Wayne | Yield (bushels/acre) Beeson |
|---|---|---|
| Control | 41.6 | 41.4 |
| Treated | 47.8 | 45.4 |

Thus, the treatment produced a yield increase of 14.9% in the Wayne soya beans and of 9.7% in the Beeson soya beans.

EXAMPLE 3

Davis soya beans were planted in plots in 30-inch rows with 5 to 7 plants per row foot. The plots were 20 feet long by 4 rows wide, and four replications were made. When the plants had reached the 5–6 leaf stage, they were sprayed with an aqueous dilution of the formulation of Example 1 at a rate of 4 oz/acre of (3-phenyl-1,2,4-thiadiazol-5-ylthio) acetic acid. The results obtained (yield in bushels/acre) compared with control plots which were not so treated were as follows:

|  | Yield (bushels/acre) | % of control |
|---|---|---|
| Control | 33.8 | 100 |
| Treated | 37.6 | 111.2 |

EXAMPLE 4

(a) A 35% w/v formulation of 1-methylheptyl (3-phenyl-1,2,4-thiadiazol-5-ylthio) acetate was prepared from the following:

| 1-methylheptyl (3-phenyl-1,2,4-thiadiazol-5-ylthio)acetate | 350 g |
|---|---|
| Arylan CA (RM 269) (from Lankro Chemicals Ltd) | 25 g |
| Sunaptol CA 200 (TS/172/74) (from Ugine Kuhlman) | 25 g |
| Solvent 200 (RM 402) (from Exxon Corporation) | 610 ml |

(b) A 35% w/v formulation of nonyl (3-phenyl-1,2,4-thiadiazol-5-ylthio) acetate was prepared from the following:

| nonyl (3-phenyl-1,2,4-thiadiazol-5-ylthio)acetate | 350 g |
|---|---|
| Arylan CA (RM 269) | 20 g |
| Sunaptol CA 200 (TS/172/74) | 30 g |
| Solvent 200 (RM 402) | 655 ml |

(c) A 35% w/v formulation of heptyl (3-phenyl-1,2,4-thiadiazol-5-ylthio) acetate was prepared from the following:

| Heptyl (3-phenyl-1,2,4-thiadiazol-5-ylthio)acetate | 350 g |
|---|---|
| Arylan CA (RM 269) | 72.5 g |
| Sunaptol CA 200 (TS/172/74) | 22.5 g |
| Solvent 200 (RM 402) | 640 ml |

EXAMPLE 5

Fiskeby 5 soya beans were sown one per pot in 3½ inch BEF pots. There were 5 pots for each of the following treatments, and the beans were grown in a glasshouse. When the plants had reached the stage when the first trifoliate leaf was fully expanded, they were sprayed with aqueous dilutions of the formulations of Example 4 at a rate of 0.5 kg of active ingredient per hectare. The plants were later assessed for growth retardation (indicative of reduced lodging) and increased branching and pod set (indicative of increased yield) in comparison with control plants which were not so treated. The results obtained were as follows:

| Formulation Example No | Stem height (% of control) | No of branches (% of control) | No of pods (% of control) |
|---|---|---|---|
| 4a | 59 | 2,800 | 101 |
| 4b | 69 | 6,000 | 106 |
| 4c | 69 | 4,200 | 108 |
| Control | 100 | 100 | 100 |

EXAMPLE 6

Soybeans were grown in plots 1 m × 10 m at 2 or 4 rows per meter. The triethanolamine salt of (3-phenyl-1,2,4-thiadiazol-5-ylthio) acetic acid was applied to the plants by spraying in aqueous solution containing Agral 60 surfactant at 2000 ppm. 240 Liters of solution per hectare were applied.

Three sets of trials were carried out, as follows:

Trial 1: two applications, one at the 3–5 leaf stage, the other at the 6–8 leaf stage, each of 0.5, 1.0, or 2.0 kg/ha a.i.

Trial 2: one application at the 3–5 leaf stage of 0.5, 1.0 or 2.0 kg/ha a.i.

Trial 3: two applications, one at the 3–5 leaf stage, the other at the 6–8 leaf stage, each of 0.125, 0.25 or 0.5 kg/ha a.i.

A sample of 5 meters of each plot was harvested for yield evaluation. Results obtained, expressed as percentage of a control plot (i.e. untreated), were as follows:

| | Trial 1 | | |
|---|---|---|---|
| | Rate a.i. applied (× 2) | | |
| Site | 0.5 | 1.0 | 2.0 |
| A | 121 | 130 | 147 |
| B | 119 | 112 | 106 |
| C | 125 | 127 | 157 |
| D | 105 | 110 | 113 |

| | Trial 2 | | |
|---|---|---|---|
| | Rate a.i. applied (× 1) | | |
| Site | 0.5 | 1.0 | 2.0 |
| E | 119 | 124 | 138 |
| F | 110 | 118 | 129 |
| G | 112 | 122 | 139 |
| H | 116 | 121 | 135 |

| | Trial 3 | | |
|---|---|---|---|
| | Rate a.i. applied (× 2) | | |
| Site | 0.125 | 0.25 | 0.5 |
| I | 105 | 110 | 118 |
| J | 108 | 112 | 120 |
| K | 104 | 113 | 125 |
| L | 103 | 108 | 117 |
| M | 103 | 116 | 129 |

We claim:

1. A method for increasing the yield of a crop of soy beans which comprises applying to the crop, after emergence thereof, an effective amount for increasing said yield, of (3-phenyl-1,2,4-thiadiazol-5-ylthio) acetic acid or the alkali metal, triethylamine, tributylamine, diethanolamine or triethanolamine salt, $C_1$ to $C_{10}$ alkyl ester or unsubstituted amide thereof.

2. A method according to claim 1 wherein the alkali metal salt is the sodium salt.

3. A method according to claim 1 wherein there is employed the triethanolamine salt.

4. A method according to claim 1, wherein the ester is formed with an alkanol of from 1 to 10 carbon atoms.

5. A method according to claim 4, wherein the ester is formed with an alkanol of from 5 to 9 carbon atoms.

6. A method according to claim 5, wherein the ester is the heptyl, 1-methylheptyl or nonyl ester.

7. A method according to claim 1 wherein the (3-phenyl-1,2,4-thiadiazol-5-ylthio) acetic acid or salt, ester or amide thereof is applied to the crop at a rate of from 1 oz to 4 lbs per acre.

8. A method according to claim 7 wherein the (3-phenyl-1,2,4-thiadiazol-5-ylthio) acetic acid or salt, ester or amide thereof is applied to the crop at a rate of from 2 oz to 1 lb per acre.

9. A method according to claim 7 wherein the (3-phenyl-1,2,4-thiadiazol-5-ylthio) acetic acid or salt, ester or amide thereof is applied to the crop at a rate of from 4 to 8 oz per acre.

10. A method according to claim 1 wherein the (3-phenyl-1,2,4-thiadiazol-5-ylthio) acetic acid or salt, ester or amide thereof is applied to the crop in the form of a composition comprising the active compound in association with a suitable vehicle.

11. A method according to claim 10 wherein the (3-phenyl-1,2,4-thiadiazol-5-ylthio) acetic acid or salt, ester or amide thereof is applied to the crop in an aqueous medium.

* * * * *